United States Patent
Matthijs-Rijsenbilt et al.

(10) Patent No.: US 6,890,708 B2
(45) Date of Patent: May 10, 2005

(54) METHOD FOR IMPROVING THE QUALITY OF SPERM FOR ARTIFICIAL INSEMINATION OF ANIMALS

(75) Inventors: Jacoba Johanna Matthijs-Rijsenbilt, Dronten (NL); Henri Woelders, Lelystad (NL)

(73) Assignee: ID-Lelystad, Instituut voor Dierhouderij en Diergezondheid B.V., Lelystad (NL)

(*) Notice: Subject to any disclaimer, the term of this patent is extended or adjusted under 35 U.S.C. 154(b) by 0 days.

(21) Appl. No.: 10/277,165

(22) Filed: Oct. 21, 2002

(65) Prior Publication Data

US 2003/0196213 A1 Oct. 16, 2003

Related U.S. Application Data

(63) Continuation of application No. PCT/NL01/00314, filed on Apr. 20, 2001.

(30) Foreign Application Priority Data

Apr. 20, 2000 (EP) .............................................. 00201444

(51) Int. Cl.[7] .............................................. A61B 17/43
(52) U.S. Cl. .............................. 435/2; 424/561; 600/35; 604/906
(58) Field of Search .......................... 424/561; 600/35; 604/906; 435/2

(56) References Cited

U.S. PATENT DOCUMENTS 6,140,121 A 10/2000 Ellington et al.

FOREIGN PATENT DOCUMENTS

| WO | WO 97 14785 | 4/1997 |
|---|---|---|
| WO | WO 99 61010 | 12/1999 |
| WO | WO 01/80867 A1 | 11/2001 |

OTHER PUBLICATIONS

Abbydeera et al., In Vitro Penetration of Pig Oocytes in a Modified Tris–Buffered Medium: Effect of BSA, Caffeine and Calcium, Theriogenology, 1997, pp. 537–534, vol. 48.
Aitken et al., Influence of Caffeine on Movement Characteristics, Fertilizing Capacity and Ability to Penetrate Cervical Mucus of Human Spermatozoa, Journal of Reproduction & Fertility, 1983, pp. 19–27, vol. 67.
Thibault, et al., Adenosine Receptor Occupancy Suppresses Chemoattractant–induced Phospholipase D Activity by Diminishing Membrane Recruitment of Small GTPases, Blood, Jan. 15, 2000, vol. 95, No. 2.
Kalab et al., Regulation of Protein Tyrosine Phosphorylation in Boar Sperm Through a cAMP–Dependent Pathway, Molecular Reproduction and Development, 1998, pp. 304–314, vol. 51.
PCT International Search Report, PCT/NL01/00314, dated Aug. 1, 2001, 4 pages.
PCT International Preliminary Examination Report, PCT/NL01/00314, dated Aug. 19, 2002, 8 pages.

*Primary Examiner*—Leon B. Lankford, Jr.
(74) *Attorney, Agent, or Firm*—TraskBritt

(57) ABSTRACT

A method and composition for artificial insemination. The method involves artificially inseminating the subject with sperm, wherein the sperm is combined or coadministered with an inhibitor of phosphodiesterase and preferably a soluble salt of an earth alkaline metal. The composition comprises phosphodiesterase inhibitor or a functional equivalent thereof, a soluble salt of an earth alkaline metal and sperm. The method and composition reduce the recruitment of polymorphonuclear neutrophils.

16 Claims, No Drawings

METHOD FOR IMPROVING THE QUALITY OF SPERM FOR ARTIFICIAL INSEMINATION OF ANIMALS

CROSS-REFERENCE TO RELATED APPLICATIONS

This application is a continuation of International Application Number PCT/NL01/00314 filed on Apr. 20, 2001, designating the United States of America corresponding to International Publication Number WO 01/80867 A1, published in English on Nov. 1, 2001, the contents of the entirety of which are incorporated by reference.

TECHNICAL FIELD

The present invention pertains to a method for improving the artificial insemination of animals, as well as a method for improving the quality and survival rate of sperm and reducing the recruitment of Polymorphonuclear Neutrophils (PMN) in the female genital tract.

BACKGROUND

When animals are bred in an industrial environment, it is desirable that the animals have predetermined or previously estimated qualities. As a consequence, there is a continuous need to improve the efficiency of breeding methods for the animals in qualitative and quantitative aspects. For instance, in cows where breeding is limited at the level of the individual animals and in pigs where breeding is limited at the level of selection lines, the improved breeding methods allows for increased efficiency of the predetermined or previously estimated qualities.

One breeding method known in the art is artificial insemination ("AI"). With artificial insemination, an ejaculate is obtained from a male animal. Portions of the ejaculate can be inseminated as obtained, can be treated to improve the quality of the ejaculate, or more doses may be obtained from the male animal for insemination. When the sperm within the ejaculate is treated, the seed is analyzed, diluted in a suitable medium such as a BTS-medium, and further treated using methods known in the art to provide a suitable sample that can be used as an inseminate.

By pre-treating and/or diluting the ejaculate, it is possible to obtain a large number of doses from the ejaculate wherein each dose can be used for insemination. For instance, 20–40 doses suitable for artificial insemination can be obtained from one pig ejaculate, wherein each a dose generally contains about 2.5 billion sperm cells. The current methods used for the artificial insemination of pigs results in fertility results of about 90% and about 11 piglets per litter.

Although these results are acceptable, it is desirable to obtain a smaller insemination dose that does not have a negative effect on the fertility result and/or the litter size. This would lead to more homogeneous animal populations and more uniform products. A more efficient insemination dose would also lead to a more efficient use of the sperm of animals and result in substantial economic advantages. Other benefits of a more efficient insemination dose include increased genetic gains in nucleus breeding such as a larger number of progeny, an increased rate of dissemination of superior traits into a population, an increased efficiency of reproduction, i.e., larger litter sizes or higher farrowing rates, and less sperm needed per insemination. The use of less sperm can be cheaper to produce since diluted semen is less expensive than more concentrated semen. The latter advantage could stimulate the use of frozen semen for routine AI, which has important veterinary health advantages (i.e., prevention of diseases).

However, one of the disadvantages of insemination, whether through natural or artificial routes, is that within hours after the insemination, the number of sperm cells in the female genital tract is dramatically reduced. The reduction in the number of sperm cells is ascribed to phagocytosis of the sperm cells by uterine leukocytes, such as Polymorphonuclear Neutrophils (PMN). Vast numbers of these PMNs are recruited to the lumen of the uterus shortly after insemination. The result is that a large amount of the inseminated sperm is not used. For instance, it has been found that after 8 hours, only about 1% of the amount of the originally artificially inseminated sperm remains and after 24 hours, only about 0.1% of the amount of inseminated sperm remains.

The phagocytosis of the sperm cells by the PMNs is why many sperm cells are needed per insemination. Moreover, the rapidly declining sperm numbers also leads to a lower fertility rate, and hence is a disadvantage of the known insemination methods. This is even more disadvantageous since the exact time of ovulation is difficult to estimate, especially with pigs. The negative effect of inseminating too early with respect to ovulation cannot be "repaired" by increasing the sperm dosage, even to as much as 6 billion sperm per dose (Steverink et al., J. Reprod. Fert. 1997, 111, 165–171) since more sperm may simply elicit more PMN recruitment and phagocytosis activity.

Thus, the combination of increased phagocytosis and the uncertainty of the exact time of ovulation leads to an even lower fertility rate. Even if the exact time of ovulation and consequently the time of insemination could be determined adequately, insemination at the right time is still of critical importance for a good fertility rate. Thus, the relatively fast phagocytosis of the sperm is still a disadvantage of the presently known insemination techniques.

There also exists a need for the improvement of fertilization techniques with respect to human in vitro fertilization. With human in vitro fertilization, it is known that improved fertilization results can be obtained by capacitation of the sperm. Capacitation is connected with a large amount of specific cellular changes in the sperm related to the ability of the sperm to the fertilization the oocyte.

Caffeine may be used to accelerate certain phases of capacitation. Caffeine stimulates the motility of sperm and aids in inducing the state of the so called "hyperactivated motility," which is seen as a specific stage of capacitation. Due to the increased motility of the sperm, the in vitro fertility rate is increased even though the lifespan of the sperm is reduced.

A major disadvantage of the capacitation of sperm is that after capacitation, the sperm has a shorter lifespan which reduces the period of time available for fertilization, or the period of time from the moment of insemination until the moment at which the sperm is no longer fertile. Thus, the use of capacitation techniques on sperm for artificial insemination with animals, such as mammals, is desirable. However, capacitation is not suitable with pigs and birds because of the shortened life expectancy of the sperm in the animals. The use of capacitation in pigs is further disadvantageous since determining the time of ovulation in pigs is difficult.

SUMMARY OF THE INVENTION

The present invention discloses a method and/or a composition which results in an improved fertility rate with insemination which may be used to make artificial insemination more efficient. A result of the prevent invention is an increased functional life span of the sperm, reduced phagocytosis of sperm and/or reduced recruitment of leukocytes.

The present invention discloses that the treatment of sperm in vitro reduces the rate at which the sperm is phagocytosed in vivo. A comparable treatment method applied to an inseminate significantly reduces the recruitment of polymorphonuclear leukocytes (i.e., neutrophil granulocytes) in vivo after artificial insemination. The treatment method comprises contacting the sperm with a phosphodiesterase inhibitor. The phosphodiesterase inhibitor may be combined with a source of a soluble salt of an earth alkaline metal, such as a soluble salt of calcium or magnesium in a suitable medium. By treating the sperm with the method described herein, the phagocytosis of sperm is strongly reduced and the presence of fertilization competent sperm in the genital tract is significantly prolonged. The sperm treatment method of the present invention is especially useful in methods for artificial insemination in pigs and other livestock species.

Since the rate at which phagocytosis normally takes place after insemination results in a reduced number of sperm in the uterus, a reduction or postponement of phagocytosis using the present invention leads to an improved fertilization rate and/or to the possibility of using lower insemination doses.

The present invention therefore comprises a method for the artificial insemination of animals including a step wherein the animal is inseminated with a composition. The composition comprises semen, a phosphodiesterase inhibitor or functional equivalent thereof and a soluble salt of an earth alkaline metal. Preferably, the soluble salt comprises a calcium source such as a soluble calcium salt.

By using the methods of the present invention, a lower dose of sperm may be used for insemination, wherein the insemination performed using the techniques of the present invention provides a similar fertilization rate as if a larger dose of sperm were used. Also, a longer interval of time between insemination and ovulation becomes permissible without significantly affecting the fertilization rates. The semen contained within the composition of the present invention has a prolonged fertility since phagocytosis of the sperm is strongly reduced. This maintains the population of sperm in the uterus at a higher level than what is found with conventional insemination. Thus, the population of sperm in the oviducts is maintained or sustained for a prolonged period of time and strongly increases the chances of fertilization.

The invention also pertains to a method for reducing the recruitment of leukocytes within an artificially inseminated mammal by adding a phosphodiesterase inhibitor or functional equivalent thereof and a calcium salt to the inseminate.

PCT International Patent Publication No. WO 97/14785 discloses the use of polysaccharides and other substances, or combinations thereof, that help to achieve the isolation of functionally superior sperm or that helps increase the survival of sperm. The disclosed substances may be used in combination with a host of other substances or techniques known in the art. Possible substances include caffeine and pentoxifilline that may be added to boost the motility of the sperm. The use of caffeine or related compounds for stimulation of motility of spermatozoa has been reported earlier (e.g., Aitken R J, et al., Journal of Reproduction and Fertility 67 19–27), however, not for increasing the life span of the sperm or for reducing PMN recruitment.

Known media for artificial insemination generally include salt-containing solutions. Examples include Beltsville TS (BTS), Modified Modena (MM), X-cell and Vital (Instruments Medicine Vérinaire, L'Aigle, France), MR-A, Kiev, Beltsville Liquid, Zorlesco, IVT, Modena, Bütschwil, BW25, or Androhep (Weitze, K F, 1991, Long-term storage of extended boar semen. In: Boar Semen Preservation II, L. A. Johnson and D. Rath, Eds. Proceedings of the 2nd International Conference on Boar Semen Preservation; Reproduction in Domestic Animals Supplement 1, 145–164; Johnson-I A; Aalbers-J G; Grooten-H J G. Artificial insemination of swine: Fecundity of boar semen stored in Beltsville TS (BTS), Modified Modena (MM) or MR-A and inseminated on one, three and four days after collection. Zuchthygiene, 1988, 23: 2, 49–55; Johnson-L A; Aalbers-J G Artificial insemination of swine: fertility using several liquid semen diluents. Proceedings of the 8th International Pig Veterinary Society Congress, Belgium, Aug. 27–31, 1984. 1984, University Faculty of Veterinary Medicine; Ghent; Belgium; Johnson-LA; Aalbers-J G; Willems-C M T; Rademaker-J H M; Rexroad-C E Jr. Use of boar spermatozoa for artificial insemination. III. Fecundity of boar spermatozoa stored in Beltsville liquid and Kiev extenders for three days at 18° C. Journal-of-Animal-Science, 1982, 54: 1, 132–136; Johnson-L A; Aalbers-J G; Willems-C M T; Rademaker-J H M. Fertility of boar semen stored in BL-1 and Kiev extenders at 18 deg C. for three days. Proceedings of the International Pig Veterinary Society 6th Congress, Copenhagen, Jun. 30–Jul. 3, 1980. 1980, 33.

Most of the media described above are intended for use in pigs. For bovine animals, a tris-citrate-yolk medium and other media are known. Other media used for other species are known in the art and it will be apparent by those of ordinary skill in the art to find suitable media for artificial insemination without exercising any inventive experimentation.

The known media described herein do not contain calcium. Further, the media described herein generally contain chelators such as $Na_2EDTA$ and/or sodium citrate. These substances are thought to bind divalent and trivalent cations and thus, keep the free calcium and magnesium concentrations very low.

The amount of added calcium salt, or equivalent thereof, is such that the chelators, which may optionally be present in conventional or commercial media, are saturated. By saturating the chelators with calcium salt, there are virtually no free chelators present in the media such that unchelated calcium is present in the media.

In one embodiment of the present invention, the earth alkaline metal salt is added to the insemination media in an amount of up to 100 mmol per liter of inseminate, preferably from 0.01 to 50 mmol of added earth alkaline metal ions per liter of inseminate.

In another embodiment of the present invention, the calcium salt is added to the insemination media in an amount of up to 10 mmol per liter of inseminate, preferably from 0.1 to 8 mmol of added calcium ions per liter of inseminate.

In another embodiment, the calcium ion source is added to the composition for insemination in an amount of 5 mmol of added calcium chloride per liter of inseminate, with higher preference from about 0.1 to 4 mmol of added calcium chloride per liter of inseminate.

The phosphodiesterase inhibitor (PDE) used in the composition of the present invention is caffeine. Other phosphodiesterase inhibitors that may be used in the methods of the present invention include other xanthine based compounds, such as theophylline, theobromine, isobutylmethylxanthine or papaverine.

It is thought that PDEs reduce the decomposition of cAMP (cyclic Adenosine MonoPhosphate). Increasing the concentration of cAMP may also be achieved by adding cAMP or using compounds that stimulate the formation of cAMP. Compounds that stimulate the formation of cAMP may do so by stimulating the enzyme adenylate cyclase (AC stimulator). An example thereof is dibutyryl cAMP.

Adding cAMP inhibits the phagocytosis of sperm in vitro. Within the boundaries of the present invention, PDEs and cAMP increasing compounds or compositions thereof are considered as functional equivalents. Accordingly, PDEs can be replaced wholly or partially by other compounds or compositions that increase the amount of cAMP.

In one embodiment, the PDE inhibitor is at least partially replaced by a compound that increases the amount of cAMP. In another embodiment of the present invention, the cAMP-increasing compounds are purines, unspecific PDE inhibitors, specific $PDE_3$ inhibitors, or synthetic membrane permeable cAMP. For a review of PDE inhibitors, see Perry M J and Higgs G A (1998) Chemotherapeutic potential of phosphodiesterase inhibitors *Curr. Opin. Chem. Biol.* 2 472–481. A purine is hypoxanthine or adenosine. Unspecific PDE-inhibitors are non-selective inhibitors that inhibit all types of PDE's, e.g., IBMX, theophylline (1,3-Dimethylxanthine), caffeine (1,3,7-Trimethylxanthine), or SQ2O,006 (1-ethyl-4-hydrazino-14-pyrazolo-3,4-b)-pyridine-5-carboxylicacidethylester). Examples of specific $PDE_3$ inhibitors include milrinone, cilostamide, amrinone, enoximone, lixazinone and indolidan.

In another embodiment, the caffeine is added to a composition comprising sperm in an amount of up to about 10 mmol per liter of inseminate, about 5 mmol per liter, or in an amount of about 0.1 to 3 mmol per liter of inseminate. The upper limit of the amount of caffeine that can be added is about 10 mmol per liter; however, when other phosphodiesterase inhibitors are used, this upper limit may fluctuate. Depending on the PDE, functional derivative or combination thereof, the effective amount may vary. It is envisaged that, depending on the activity of the PDE or functional derivative thereof, the amount of PDE or functional equivalent thereof added to the composition comprising sperm may vary from about 0.01, 0.1, 0.5, 1, 2, 3, 4, 5, 6, 7, 8, 9, 10 mmol per liter of inseminate, or up to about 20, 30, 40, 50, 60, 70, 100 mmol per liter of inseminate. The ranges may be determined by one of ordinary skill in the art using the experiments disclosed in the Examples described herein. The upper limit for the phosphodiesterase inhibitor or functional equivalent thereof is the amount that avoids an unwanted or undesired toxic effect on the inseminated animal using the phosphodiesterase inhibitor.

In a further aspect, other routes can be used to inhibit phagocytosis of sperm after insemination in addition to using PDE inhibitors or adenylate cyclase stimulants. These alternatives are included in the functional equivalents of the PDEs in the light of the present invention. One route is the masking of the ligands involved in binding of PMN to spermatozoa. It is known that sperm can bind opsonins, e.g., antibodies that allow the subsequent binding of the PMNs. Live, intact sperm possess intrinsic ligands that allow binding by PMN. For the latter class of ligands, no prior opsonization is necessary to allow for the immediate start of phagocytosis after insemination. These ligands use sugar moieties for binding with PMN. Therefore, the following methods may also be used to inhibit phagocytosis:

masking of the ligands, e.g., by adding a complementary carbohydrate binding molecule; and enzymatic degradation of the ligand, e.g., by using deglycosylating enzymes or agents.

Masking of the ligands is used herein. The phagocytosis of boar spermatozoa in vitro by PMN is inhibited strongly by adding polysulphated polymers, e.g. glycosaminoglycans such as heparin, due to the binding of these substances to the plasma membrane and shielding of the ligands involved in binding by PMN.

Another way to inhibit phagocytosis of sperm is to capacitate the sperm. It was found that treating the semen, for example in vitro, with capacitation strongly reduced the phagocytosis of sperm by PMNs, in particular in vitro. Capacitation is considered to be a series of cellular changes, notably changes of the surface of the cell membrane, and involving deglycosylation of membrane proteins and membrane lipids, by which the spermatozoa acquire the ability to penetrate and fertilize the oocyte. The ligands involved in phagocytosis are lost, and the ability to bind serum-derived opsonins is decreased.

The phosphodiesterase inhibitors or functional equivalents thereof can be added to the composition comprising sperm at any moment prior to insemination. Suitable moments for adding the phosphodiesterase inhibitor include directly after collecting the ejaculate or during the processing of the ejaculate to dosages in a form and amount suitable for artificial insemination. The phosphodiesterase inhibitor, such as caffeine, can be added to the composition comprising sperm directly prior to the insemination. If a combination of calcium and caffeine is used, the calcium and caffeine are added to the composition immediately prior to insemination.

Another embodiment includes a composition comprising calcium and caffeine that is applied directly after the insemination with a conventional insemination dosage. In this embodiment, the insemination with a composition comprising sperm is directly followed by another step in which a composition comprising calcium and caffeine are administered. It is also possible to first administer a composition comprising calcium ions and the PDE inhibitor, and thereafter carrying out the insemination step.

In another aspect, an increased fertility rate is obtained when the sperm cells are administered to the animal in a suitable medium, followed by the administration of a solution containing caffeine and calcium salt to the animal. This aspect of the present invention provides an increased fertility rate when compared to administering a similar volume of a solution which contains sperm together with caffeine and the calcium salt.

In vivo experiments where female mammals were inseminated with a dosage of sperm in a conventional medium, followed by administration of a dose of caffeine and calcium salt in a suitable medium, results in a reduced rate of the recruitment of leukocytes and reduced phagocytosis was found.

Administration of a composition comprising phosphodiesterase inhibitor or a functional equivalent thereof and a calcium salt after conventional insemination, may also lead to an improved fertility rate in certain animals and is within the scope of the invention.

Storage of the treated inseminate for several days prior to the use thereof has a less positive influence on the life span of the sperm. Therefore, it is desirable to add the phosphodiesterase and calcium ions to the sperm immediately prior to the insemination. A composition including the phosphodiesterase inhibitor or functional equivalent thereof and the calcium ions in a separate holder is also within the scope of the present invention. Another composition comprising the sperm composition may be provided in another separate holder. The two compositions in the two separate holders can be mixed directly prior to insemination of the animal. Accordingly, the present invention also encompasses a kit comprising a first holder including the phosphodiesterase inhibitor or functional equivalent thereof and calcium. In another embodiment, a kit with the first holder including the phosphodiesterase inhibitor or functional equivalent thereof and calcium and a second holder with a composition including sperm is disclosed.

A method according to the present invention is suitable for all types of sperm and is applicable to all types of animals, including without limitation humans, mammals, birds and pigs. By applying the method of the present invention to pig sperm, the amount of sperm and inseminate may be considerably reduced without lowering the fertility rate. The method of the present invention also allows a larger number of sperm doses to be obtained from one ejaculate which promotes the homogeneity of the population. Likewise, it is possible to use a conventional amount of sperm in the inseminate in a method according to the invention to obtain an improved fertility rate.

DETAILED DESCRIPTION OF THE INVENTION

The invention is further explained by the use of the following illustrative examples.

EXAMPLE I

The influence of caffeine and caffeine plus $Ca^{2+}$ on phagocytosis of sperm by PMN in vitro.
Materials and Methods.
Media.

Tyrode's medium was used as described as "standard Tyrode's medium" in Harkema et al. (Harkema, W, Harrison, R A P, Miller, N G A, Topper, E K, and Woelders, H, 1998, Enhanced Binding of Zona Pellucida Proteins to the Acrosomal Region of Intact Boar Spermatozoa in Response to Fertilizing Conditions: A Flow Cytometric Study. Biology of Reproduction, 58, 421–430), but without propidium iodide and lacking bovine serum albumin (BSA). The medium was also supplemented with 15% (v/v) sow serum treated to heat-inactivate complement. Serum was prepared from blood collected from 11 primiparous sows, pooled, and frozen in aliquots at −80° C.
Isolation and Preparation of PMN.

Per experiment, 20 ml peripheral blood of a single Dutch Landrace sow (each experiment a different sow) was collected in heparinized vacutainers (Venoject, Omnilabo, Breda, The Netherlands). The peripheral blood was subsequently diluted with an equal volume of phosphate buffered saline (PBS). A number of 15-ml screw-capped polypropylene centrifuge tubes were filled with 3 ml Ficoll Paque (Pharmacia, Biotech Benelux, Roosendaal, The Netherlands). 4 ml of diluted blood was carefully layered into each tube over the Ficoll and centrifuged at 400×g for 35 min. The supernatant, including the mononuclear cells at the interface, was removed. The pellet was resuspended in 2 ml of ice-cold distilled water to lyse the erythrocytes. Isotonicity was restored after 45 s by adding 1 ml of 27 g $I^{-1}$ NaCl. The PMNs were pelleted by centrifugation for 10 min at 400×g and the lysis procedure was repeated. Each PMN pellet was washed two more times more in 5 ml PBS, and resuspended in 1 ml PBS. All cell suspensions were pooled together, mixed well, and subjected to centrifugation. The PMN were resuspended in TM-s with inactivated complement, and the cell concentration was determined using a hemocytometer. The PMN preparation was stored overnight at 4° C. Prior to use, the PMN suspension was mixed and centrifuged at 400×g for 10 min. The PMN were resuspended in TM-s with inactivated complement and adjusted to 10×10$^6$ cells ml$^{-1}$. The PMN isolation procedure yielded a preparation containing more than 90% granulocytes, of which about 85% were neutrophils. The viability, assessed by trypan blue exclusion, was >98%.
Preparation of Semen Samples.

Semen was obtained from Dutch A.I. stations. Per experiment, semen was used from a single Yorkshire breeding boar (each experiment a different boar). At the AI-station, the semen was diluted to a concentration of approximately 30×10$^6$ cells/ml in Beltsville Thawing Solution (BTS) (Johnson et al., 1988). The diluted semen was stored at 17° C. for up to 48 hours, until the diluted semen sample was used.

The diluted semen in BTS was stained at room temperature with 10 $\mu$mol $I^{-1}$ of the DNA-binding fluorescent dye Hoechst 33342 (Sigma, Brunschwig chemie, Amsterdam, The Netherlands) for at least 30 min. 3 ml of the semen was washed by centrifugation through two layers of 35% and 70% (v/v) Percoll (Sigma) in saline, respectively (Harrison et al., 1993). The pelleted sperm was resuspended in TM and the sperm concentration was adjusted to 20×10$^6$ cells ml$^{-1}$ with TM using a hemocytometer.
Phagocytosis Assay.

Aliquots of 80 $\mu$l of the PMN suspension (see, PMN isolation and preparation of PMNs) in TM or TM-s, with either intact or inactivated complement, were transferred to a 96-well polystyrene microtest plate. To each well, 20 $\mu$l of sperm suspension (see, preparation of semen samples) was added and the microtest plate was placed in a humidified incubator at 38° C. with 5% $CO_2$ in air. The final concentrations of PMN, sperm, and serum were 8×10$^6$ ml$^{-1}$, 4×10$^6$ ml$^{-1}$, and 12% (v/v), respectively. The samples were incubated with gentle swirling on a test plate shaker. After 15, 30, 45, 60 or 90 min., samples were quantitatively transferred into tubes containing an equal volume of 40 mg ml$^{-1}$ heparin (Sigma) in PBS. The heparin facilitates dissociation of agglutinated PMNs. The samples were thoroughly mixed, left for 15 min., and mixed again. Subsamples of 75 $\mu$l were fixed by addition of 25 $\mu$l of 2% (v/v) glutaraldehyde (Fluka, Brunschwig chemie, Amsterdam, The Netherlands) in PBS. "Blank" samples, i.e., sperm without PMNs (80 $\mu$l TM-s mixed with 20 $\mu$l sperm suspension), were incubated in parallel to monitor sperm survival during the treatment. "Reference" samples, i.e., frozen-thawed (killed) semen, were incubated in parallel with the PMNs as a reference for the phagocytotic activity of the PMNs. The frozen-thawed semen was taken from a large stock of semen from one ejaculate and washed 3 times in PBS prior to use.
Microscopic Evaluation of Phagocytosis and Sperm Viability.

For evaluation of phagocytosis, wet mounts of the fixed samples were examined with a combination of phase-contrast and fluorescence microscopy (Olympus BH2, Tokyo, Japan) at 400× magnification. The mounts enabled observation and counting of fluorescently labeled spermatozoa inside and outside the phagocytes. By focusing at different levels in the mount, spermatozoa that were located above or below the PMN could be distinguished from those that were phagocytosed. In many PMNs that had ingested a spermatozoon, the presence of the sperm nucleus or tail caused a conspicuous change of the shape of the PMN. Two hundred spermatozoa were evaluated and classified as inside or outside the PMN (i.e., phagocytosed or not phagocytosed). The same fixed mounts were used to assess the acrosome morphology of the non-phagocytosed spermatozoa at the moment of fixation. One hundred cells were classified using phase-contrast microscopy at 400× magnification, as NAR (normal apical ridge), NAR' (slightly altered normal apical ridge), DAR (damaged apical ridge), MAR (missing apical ridge) and LAC (loose acrosomal cap), as described by Pursel et al. (Pursel V G, Schulman L L and Johnson L A, 1978, Distribution and morphology of fresh and frozen-thawed sperm in the reproductive tract of gilts after insemination Biology of Reproduction 19 69–76.)

Results.

Experiment 1

The semen was stored for 48 hours in BTS at 17° C.

In vitro phagocytosis of sperm by PMN.

I. Without Pre-incubation:

|  | % of phagocytosed sperm | | |
|---|---|---|---|
| Control | 64 | 78 | 71 |
| Caffeine 1 mM | 20 | 22 | 18 |

II. After Pre-incubation:

|  | % of phagocytosed sperm | | | |
|---|---|---|---|---|
| Phagocytosis time | 15 min | 30 min | 60 min | 90 min |
| Control | 62 | 60 | 70 | 69 |
| Control pre-inc.* | 49 | 55 | 68 | 71 |
| Db-cAMP[1] 0.1 mM pre-inc.* | 35 | 59 | 60 | 65 |
| Caffeine 2 mM pre-inc.* | 22 | 15 | 29 | 20 |
| Db cAMP 0.2 mM pre-inc.* | 47 | 47 | 58 | 54 |

[1]Db-cAMP = dibutyryl-cAMP
*Preincubated during 30 min. at 38° C.

Sperm viability: After adding active compound and pre-incubation at 38° C.:

|  | % motile sperm | % NAR-DAR-MAR-LAC, respectively |
|---|---|---|
| Control | 60 | 68-23-01-08 |
| Control pre-inc.* | 60 | 61-32-00-07 |
| Db-cAMP pre-inc.* | 60 | 67-23-02-08 |
| Caffeine pre-inc.* | 60 | 53-30-02-15 |

*Preincubated during 30 min. at 38° C.

Sperm viability: In blank samples, i.e., after adding the active compound, after pre-incubation at 38° C., and measured during incubation parallel to the phagocytosis incubation, but without PMN.

|  | % NAR-MAR-MAR-LAC, respectively | |
|---|---|---|
| Phagocytosis time | 30 min. | 60 min. |
| Control | 56-35-00-09 | |
| Control pre-inc.* | 56-34-00-10 | |
| Db cAMP pre-inc.* | 56-36-02-06 | |
| Caffeine pre-inc.* | 37-39-03-21 | |
| Db cAMP (2x) | 54-36-02-08 | |
| Control |  | 44-40-04-12 |
| Caffeine |  | 37-36-05-22 |

*Preincubated during 30 min. at 38° C.

Experiment 2

Phagocytosis of sperm; mean of duplicates.

I. Without Pre-incubation:

| Time (min.) | 15 | 30 | 60 | 15 | 30 | 60 |
|---|---|---|---|---|---|---|
|  | % phagoc. sperm | | | % inhibition* | | |
| 0 mM caffeine | 53 | 76 | 77 | — | — | — |
| 0.2 mM caffeine | 48 | 73 | 75 | 9 | 4 | 3 |
| 0.5 mM caffeine | 40 | 67 | 68 | 25 | 12 | 12 |
| 1 mM caffeine | 29 | 58 | 62 | 45 | 24 | 19 |
| 2 mM caffeine | 28 | 51 | 56 | 47 | 33 | 27 |

II. After Pre-Incubation:

| Time (mm.) | 15 | 30 | 60 | 15 | 30 | 60 |
|---|---|---|---|---|---|---|
|  | % phag. Sperm | | | % inhibition* | | |
| 0 mM caffeine | 47 | 64 | 63 | — | — | — |
| 0.5 mM caffeine | 29 | 28 | 42 | 38 | 56 | 33 |
| 1 mM caffeine | 14 | 26 | 24 | 70 | 59 | 62 |
| 2 mM caffeine | 9 | 17 | 21 | 81 | 73 | 67 |

* Percentage decrease of phagocytosis relative to control

Sperm viability: After adding active compound.
I. Without Pre-incubation:

| caffeine | % motile sperm | % NAR-DAR-MAR-LAC |
|---|---|---|
| 0 mM | 80 | 85-10-01-04 |
| 0.2 mM | 80 | 84-12-01-03 |
| 0.5 mM | 80 | 84-12-02-02 |
| 1 mM | 80 | 87-09-01-03 |
| 2 mM | 80 | 82-13-01-04 |

II. After Pre-incubation:

|  | % motile sperm | % NAR-DAR-MAR-LAC |
|---|---|---|
| 0 mM | 80 | 82-14-01-04 |
| 0.5 mM | 80 | 83-14-01-02 |
| 1 mM | 80 | 77-16-01-06 |
| 2 mM | 80 | 73-20-02-05 |

Sperm viability: In blank samples, i.e., after adding the active compound, after pre-incubation at 38° C. (when used), and measured during incubation parallel to the phagocytosis incubation, but without PMN.

I. Without Pre-incubation:

| Phagocytosis time 30 min. Caffeine | % NAR-DAR-MAR-LAC, respectively |
|---|---|
| 0 mM | 83-13-00-04 |
| 0.2 mM | 85-12-00-03 |
| 0.5 mM | 87-10-00-03 |
| 1 mM | 85-10-00-05 |
| 2 mM | 79-12-01-08 |

II. After Pre-incubation:

| Caffeine | % NAR-DAR-MAR-LAC, respectively |
|---|---|
| 0 mM | 85-11-00-04 |
| 0.5 mM | 85-12-01-02 |
| 1 mM | 72-21-01-06 |
| 2 mM | 70-24-01-05 |

Experiment 3

Phagocytosis of sperm; mean of duplicates after pre-incubation of sperm for 30 min. at 38° C. with and without 1 mM caffeine:

| Time(min.) | 15 | 30 | 60 | 15 | 30 | 60 |
|---|---|---|---|---|---|---|
| | % phag. sperm | | | % inhibition* | | |
| 0 mM caffeine | 56 | 71 | 79 | — | — | — |
| 1 mM caffeine | 32 | 45 | 56 | 43 | 37 | 29 |
| Reference | 51 | 67 | 76 | | | |

*Percentage decrease of phagocytosis relative to control

Sperm viability: After pre-incubation of sperm for 30 min. at 38° C. with and without 1 mM caffeine.

| | % motile sperm | % NAR-DAR-MAR-LAC |
|---|---|---|
| 0 mM caffeine | 75 | 74-14-02-10 |
| 1 mM caffeine | 65 | 67-24-01-08 |
| reference | 75 | 78-16-02-04 |

Sperm viability: In blank samples, i.e., after adding the active compound, after pre-incubation at 38° C. and measured during incubation parallel to the phagocytosis incubation, but without PMN.

| Phagocytosis time 30 min. | % NAR-DAR-MAR-LAC |
|---|---|
| 0 mM caffeine | 73-21-01-05 |
| 1 caffeine | 66-24-02-08 |
| Reference | 72-24-01-04 |

Experiment 4

Inhibition of phagocytosis of sperm by addition of caffeine or caffeine plus Ca2+ to the semen extender, the day before use.

This experiment shows that it is possible to add the caffeine after collection of the semen. The augmentation of the effect of caffeine by supplying calcium is also shown.

The semen was extended with regular BTS or with BTS plus 6 mM of $CaCl_2$. The semen also received 0, 0.2 or 1 mM caffeine. The semen was stored for 24 hours at 17° C. Pre-incubation of the semen at 38° C. before the challenge with the PMN was used to mimic the situation of the semen after insemination into the sow. The experiment shows that the caffeine inhibits phagocytosis after one day.

% Phagocytosed sperm (mean of duplicates):

I. Without Pre-incubation:

| Time (min.) | 15 | 30 | 60 | 15 | 30 | 60 |
|---|---|---|---|---|---|---|
| | % phag. Sperm | | | % inhibition* | | |
| Regular BTS | 68 | 76 | 82 | — | — | — |
| BTS + 0.2 mM Caf | 70 | 81 | 75 | — | — | — |
| BTS + 1 mM Caf | 58 | 59 | 67 | 17 | 22 | 19 |
| BTS/Ca[1] | 64 | 71 | 78 | 7 | 7 | 5 |
| BTS/Ca + 0.2 mM Caf | 63 | 73 | 76 | 9 | 5 | 7 |
| BTS/Ca + 1 mM Caf | 53 | 53 | 63 | 23 | 31 | 24 |

II. After Pre-incubation for 30 Min. at 38° C.:

| Time (min.) | 15 | 30 | 60 | 15 | 30 | 60 |
|---|---|---|---|---|---|---|
| | % phag. Sperm % | | | % inhibition* | | |
| Regular BTS | 67 | 62 | 66 | — | — | — |
| BTS + 0.2 mM Caf | 59 | 52 | 68 | 13 | 16 | — |
| BTS + 1 mM Caf | 51 | 42 | 53 | 23 | 33 | 20 |
| BTS/Ca[1] | 66 | 66 | 64 | 2 | — | 3 |
| BTS/Ca + 0.2 mM Caf | 61 | 59 | 59 | 10 | 5 | 11 |
| BTS/Ca + 1 mM Caf | 33 | 34 | 57 | 50 | 54 | 14 |

*Percentage decrease of phagocytosis relative to control
[1]BTS plus 6 mM $CaCl_2$ Viability of the sperm after 24 hour storage and after pre-incubation (when used):

I. Without Pre-incubation:

| | % motile sperm | % NAR-DAR-MAR-LAC |
|---|---|---|
| Regular BTS | 75 | 68-27-00-05 |
| BTS + 0.2 mM Caf | 75 | 69-27-00-04 |
| BTS + 1 mM Caf | 70 | 58-38-00-04 |
| BTS/Ca[1] | 70 | 65-29-01-05 |
| BTS/Ca + 0.2 mM Caf | 70 | 59-35-01-04 |
| BTS/Ca + 1 mM Caf | 70 | 59-39-00-03 |

II. After Pre-incubation:

| | % motile sperm | % NAR-DAR-MAR-LAC |
|---|---|---|
| Regular BTS | 75 | 69-27-01-03 |
| BTS + 0.2 mM Caf | 75 | 75-22-00-03 |
| BTS + 1 mM Caf | 70 | 72-23-00-05 |
| BTS/Ca[1] | 65 | 69-26-00-05 |
| BTS/Ca + 0.2 mM Caf | 65 | 70-25-00-05 |
| BTS/Ca + 1 mM Caf | 65 | 65-25-01-09 |

[1]BTS plus 6 mM $CaCl_2$

Sperm viability: In blank samples, i.e., measured during incubation parallel to the phagocytosis incubation, but without PMN.

I. Without Pre-incubation:

| Phagocytosis time: 30 min. | % NAR-DAR-MAR-LAC |
|---|---|
| Regular BTS | 69-22-00-09 |
| BTS + 0.2 mM Caf | 73-19-01-07 |
| BTS + 1 mM Caf | 71-17-01-11 |
| BTS/Ca[1] | 70-17-01-12 |
| BTS/Ca + 0.2 mM Caf | 65-21-01-13 |
| BTS/Ca + 1 mM Caf | 57-29-01-13 |

II. After Pre-incubation:

| Phagocytosis time: 30 min. | % NAR-DAR-MAR-LAC |
|---|---|
| Regular BTS | 64-19-03-14 |
| BTS + 0.2 mM Caf | 58-26-01-14 |
| BTS + 1 mM Caf | 43-34-01-22 |
| BTS/Ca[1] | 63-23-00-14 |
| BTS/Ca + 0.2 mM Caf | 66-21-00-14 |
| BTS/Ca + 1 mM Caf | 48-33-00-19 |

[1]BTS plus 6 mM CaCl$_2$

Experiment 5

The semen was stored for 24 hours at 17° C. in regular BTS plus CaCl$_2$, but without caffeine. Prior to the phagocytosis assay, the semen was mixed with an equal volume of BTS plus 6 mM CaCl$_2$ and Caffeine.

The experiment showed that the addition of 1 mM caffeine reduced the phagocytosis of sperm by PMN in vitro, without adversely affecting sperm viability. The effect was augmented by the presence of calcium ions and by pre-incubation at 38° C. during 30 minutes.

% Phagocytosed sperm (mean of duplicates):
I. Without Pre-incubation:

| Time (min.) | 15 | 30 | 60 | 15 | 30 | 60 |
|---|---|---|---|---|---|---|
| | % phag. Sperm % | | | % inhibition* | | |
| Regular BTS | 68 | 73 | 76 | | | |
| BTS + 0.2 mM Caf | 70 | 72 | 76 | — | 1 | — |
| BTS + 1 mM Caf | 62 | 59 | 65 | 9 | 19 | 14 |
| BTS/Ca[1] | 65 | 68 | 78 | 4 | 7 | — |
| BTS/Ca + 0.2 mM Caf | 66 | 63 | 75 | 3 | 14 | 1 |
| BTS/Ca + 1 mM Caf | 46 | 43 | 66 | 37 | 41 | 13 |

II. After Pre-incubation for 30 Min. at 38° C.:

| Time (min.) | 15 | 30 | 60 | 15 | 30 | 60 |
|---|---|---|---|---|---|---|
| | % phag. Sperm % | | | % inhibition* | | |
| Regular BTS | 57 | 64 | 75 | — | — | — |
| BTS + 0.2 mM Caf | 55 | 63 | 59 | 3 | 2 | 29 |
| BTS + 1 mM Caf | 34 | 41 | 35 | 40 | 37 | 53 |
| BTS/Ca[1] | 51 | 55 | 67 | 10 | 14 | 11 |
| BTS/Ca + 0.2 mM Caf | 58 | 54 | 64 | — | 16 | 15 |
| BTS/Ca + 1 mM Caf | 21 | 19 | 31 | 64 | 71 | 59 |

*Percentage decrease of phagocytosis relative to control
[1]BTS plus 6 mM CaCl$_2$ Viability of the sperm after 24 hour storage in regular BTS, followed by mixing with equal volume of regular or modified BTS, and 30 min. pre-incubation at 38° C. (when used):

I. Without Pre-incubation:

| | % motile sperm | % NAR-DAR-MAR-LAC |
|---|---|---|
| Regular BTS | 75 | 70-27-00-03 |
| BTS + 0.2 mM Caf | 75 | 76-19-01-04 |
| BTS + 1 mM Caf | 75 | 64-28-01-07 |
| BTS/Ca[1] | 75 | 72-22-00-06 |
| BTS/Ca + 0.2 mM Caf | 75 | 63-33-01-03 |
| BTS/Ca + 1 mM Caf | 70 | 65-27-01-07 |

II. After Pre-incubation:

| | % motile sperm | % NAR-DAR-MAR-LAC |
|---|---|---|
| Regular BTS | 70 | 71-23-01-05 |
| BTS + 0.2 mM Caf | 75 | 66-30-01-03 |
| BTS + 1 mM Caf | 65 | 69-24-00-07 |
| BTS/Ca[1] | 60 | 70-25-00-05 |
| BTS/Ca + 0.2 mM Caf | 65 | 67-26-01-06 |
| BTS/Ca + 1 mM Caf | 60 | 70-24-01-05 |

[1]BTS plus 6 mM CaCl$_2$

Sperm viability: In blank samples, i.e., measured during incubation parallel to the phagocytosis incubation, but without PMN.
I. Without Pre-incubation:

| Phagocytosis time: 30 min. | % NAR-DAR-MAR-LAC |
|---|---|
| Regular BTS | 62-28-01-09 |
| BTS + 0.2 mM Caf | 70-13-01-16 |
| BTS + 1 mM Caf | 57-21-00-22 |
| BTS/Ca[1] | 69-17-00-14 |
| BTS/Ca + 0.2 mM Caf | 67-22-00-11 |
| BTS/Ca + 1 mM Caf | 66-22-01-12 |

II. After Pre-incubation:

| Phagocytosis time: 30 min. | % NAR-DAR-MAR-LAC |
|---|---|
| Regular BTS | 65-17-00-17 |
| BTS + 0.2 mM Caf | 70-15-01-14 |
| BTS + 1 mM Caf | 62-18-00-20 |
| BTS/Ca[1] | 70-18-00-12 |
| BTS/Ca + 0.2 mM Caf | 67-18-00-15 |
| BTS/Ca + 1 mM Caf | 66-22-01-11 |

[1]BTS plus 6 mM CaCl$_2$

EXAMPLE II

The effect of phosphodiesterase inhibitors, CaCl$_2$ and sodium EDTA on sperm phagocytosis by PMN.
Materials and Methods
Experimental Design:

Oestrus sows were inseminated with H33342 labeled semen and either:
(1) 1 billion sperm in 80 ml BTS (reference);
(2) 1 billion sperm in 40 ml BTS with 2.3 mM caffeine in 40 ml BTS in which the sodium EDTA was replaced by 6 mM CaCl$_2$ (BTS–Caf/Ca); or
(3) 1 billion sperm in 80 ml BTS with 25 mM sodium EDTA instead of 3.4 mM (BTS–EDTA).

Within an experiment day, two sows per treatment were used. The experiment days were replicated three times resulting in six sows per treatment. Per experiment day, one single ejaculate of semen was used. Boar A was used for one experiment day and boar B was used for two experiment days.

Oestrus Synchronization and Detection.

Per experiment day, 8 Multiparous Dutch Landrace× Yorkshire sows (parity ranging from 3–12) were purchased from a Dutch breeding farm. At the day of weaning, the sows were transported to and individually housed at a mechanically ventilated pig facility at the Institute for Animal Health and Science in Lelystad. After 4 days, approximately 26–27 hours before insemination, each sow received an intramuscular injection of 750 IU HCG (AUV, Cuijk) for synchronization of ovulation. Early in the morning of the day of insemination, about 15 hours before ovulation was expected, oestrus detection was performed by consecutively allowing the sows to contact a mature boar in his pen. Per experiment day, the 6 sows which exhibited a distinct standing heat reflex when mounted by the boar were selected for the experiment, and the 6 sows were randomly assigned to the three treatment groups.

Preparation of the Semen.

The day before insemination, semen was collected from a Yorkshire breeding boar with proven fertility at the AI station in Bunnik, where the initial sperm concentration was assessed by measuring light scattering at 550 nm. An aliquot of about 8 billion spermatozoa was diluted with an equal volume of BTS (Johnson L A, Aalbers J G and Grooten H J G (1988) Artificial insemination of swine: fecundity of boar semen stored in beltsville TS (BTS), modified modena (MM), or MR-A and inseminated on one, three and four days after collection Zucht hygiene 23 49–55) and transported in a refrigerated box at 17° C. to the institute in Lelystad. In a 17° C. room, 3 aliquots of semen with a volume corresponding to 2 billion sperm, were diluted with wither BTS at a volume of 80 ml or 160 ml or with modified BTS containing 25 mM sodium EDTA instead of 3.36 mM (BTS–EDTA) to a volume of 160 ml (final EDTA concentration was approximately 23 mM). The three semen preparations were stained by adding the membrane-permeable DNA-binding fluorescent dye Hoechst 33342 (Sigma, Brunswich chemie, Amsterdam) to a concentration of 10 $\mu$M. The preparations were covered and stored overnight at 17° C. The next day, small samples were withdrawn for the evaluation of viability and to determine the sperm concentration. The three sperm preparations were each divided equally over two insemination flasks. All semen was transported in an isolated box to the pig facility, and combined with two insemination flasks. Each insemination flask contained 40 ml of a solution of 2.3 mM caffeine (Sigma) in modified BTS, wherein the sodium EDTA was omitted and contained 6 mM calcium chloride (BTS–Caf/Ca).

Evaluation of Sperm Viability.

The percentage of motile spermatozoa was estimated at 38° C. using phase-contrast microscopy at 100× magnification. After fixation with glutaraldehyde (Fluka, Brunswich chemie, Amsterdam), acrosome morphology was assessed using phase-contrast microscopy at 400× magnification. 2×100 spermatozoa were classified as described by Pursel et al. (Pursel V G, Schulman L L and Johnson L A, 1978, Distribution and morphology of fresh and frozen-thawed sperm in the reproductive tract of guts after insemination *Biology of Reproduction* 19 69–76).

Prior to the viability evaluations, the sample from the preparation of 2 billion sperm per 80 ml were mixed 1:1 with BTS–Caf/Ca.

The sperm concentration, or the number of sperm per insemination, had been based on the value of the semen sperm concentration provided by the AI station which was based on the measurement of light-scattering. However, to determine the sperm concentration more accurately, a small sample of each semen preparation was diluted to a final concentration of $0.7 \times 10^6$ sperm/ml in 0.1 M sodium citrate and the number of sperm was determined in a hemocytometer.

Procedures at Insemination and Slaughtering.

After oestrus detection (as described herein), the sows were successively inseminated at intervals of 35 mm with one of the six inseminate preparations (as described herein). The insemination with 1 billion sperm in 40 ml BTS was immediately succeeded by an insemination with 40 ml of BTS–Caf/Ca. The sows were inseminated through the cervix with a spiral tip catheter (Nifa Instruments, Leeuwarden, The Netherlands) lubricated with a sterile bacteriostatic jelly (Johnson & Johnson, Nifa Instruments, Leeuwarden). During insemination, back pressure was applied on the sows. Back flow of semen during, or directly after insemination was collected in a stoma bag (Combihesive, Convatec, Woerden). The stoma bag was clipped onto a ring that was fixed around the vulva of the sow with industrial cyanoacrylate glue and secured with tape. The bag was replaced with a new bag when a sow produced much back flow or had urinated into the stoma bag. The content of each stoma bag was emptied in an urine beaker, weighed on a balance (±0.05 g) and transported on ice to the laboratory for further processing.

The sows were slaughtered at 4 hours after insemination. For slaughter, a sow was moved to an adjacent room and immediately stunned by intravenous injection of 10 ml of T61 (AUV, Cuijk). The sow was exsanguinated from the neck artery. The abdomen of each sow was opened and clamps were placed at the most caudal part of the isthmus, at the junctions between uterine corpus and right horn, between cervix and corpus, between vagina and cervix, and at the caudal end of the vagina. The uterus and oviducts were dissected from their ligaments and the genital tract, with the exception of the vulva were removed as quickly as possible and transported on ice to the laboratory.

Preparation of the Samples.

Bottles containing PBS for rinsing were placed on ice. Oviducts, right uterus horn, left uterus horn plus corpus, cervix, and vagina were separated. The vagina was cut longitudinally, placed inside up in a glass dish and was massaged repeatedly in 50 ml PBS. The cervix was treated likewise in 100 ml PBS. The uterus horns were flushed by introducing 35 ml of PBS and repeatedly passing from one side to the other, and vice versa. These procedures were repeated one, two and three times for cervix, uterus horns and vagina, respectively. The parts of the genital tract were weighed and subsequently ground in a meat mill. From each tissue, a 40 g aliquot was diluted twice with PBS and homogenized in a Sorvall mixer (Meyvis & Co, Bergen op Zoom) for 5 minutes at maximum speed. Subsamples of ±10 g were stored at −20° C. The right and left oviducts, which had not been flushed, were homogenized together.

Per part of the tractus, the recovered rinse fluid was pooled, the total volume of the rinse fluid was determined, the rinse fluid was thoroughly mixed, and a 10 ml aliquot was fixed by adding 100 $\mu$l of 50% v/v glutaraldehyde (Fluka, Brunswich chemie, Amsterdam). The collected back flow (see, procedures at insemination) was handled accordingly. If the rinse fluid of the vagina or the cervix was contaminated with blood, then prior to fixation, the 10-ml sample was centrifuged and the pellet was resuspended in 2 ml of ice-cold distilled water to lyse the erythrocytes.

Isotonicity was restored after 1 min. by addition of 1 ml of 27 g/l NaCl in water. All fixed samples were stored at 4° C.

Microscopical Evaluation of the Samples.

Rinse Fluid and Semen Back Flow.

Samples were mixed prior to use. The numbers of the PMNs and the sperm inside and outside the PMNs, was determined by counting cells in a KOVA-slide hemocytometer (Instruchemie B V, Hilversum, N L), using a combination of phase-contrast and epifluorescence microscopy at 200× magnification. The cells were counted in a part of the grid corresponding to a volume of 0.444 µl. To make counting easy and reliable, the concentration of the cells in the samples was adjusted by dilution with PBS or by centrifugation, such that the sample would contain between 56 and 225 cells per µl. If the cells did not contain between 56 and 225 cells per µl, the cells in an entire grid, or several entire grids, were counted that correspond to a volume of up to 3.6 µl of sample. The phase-contrast microscopy was used to distinguish the neutrophils from other leukocytes without differential staining. May-Grunwald stained smears of pellets, obtained after centrifugation of rinse fluid and before fixation, were sometimes evaluated to check for the relative amounts of the various leukocytes in the sample. The phagocytosed fluorescent sperm nuclei inside the PMN could be clearly distinguished using combined phase-contrast and fluorescence microscopy. The percentage of phagocytosed sperm, 2×100 cells, was assessed in wet mounts at 200–400× magnification and classified as inside or outside the PMNs (i.e., phagocytosed or not phagocytosed).

Tissue homogenates: After thawing, the samples were thoroughly mixed. A small amount of the homogenate was placed on top of a Bürker Türk hemocytometer and spread under the cover-slip. The number of spermatozoa was determined within several entire 0.9 µl grids using combined phase-contrast and fluorescence microscopy at 400× magnification. Cells were counted in four counting chambers (vagina, cervix and uterus horns) or 12–16 counting chambers (oviducts) per sample. By focusing at different levels in the hemocytometer, all the fluorescent sperm in the homogenized tissue slush could be revealed.

Results.

Since one of the animals inseminated with caffeine was found to have endometritis, the data from that animal was discarded. Inspection of the ovaries showed that six out of 18 animals had ovulated, or were in the process of ovulation, whereas the others had not yet ovulated. The number of PMN or sperm recovered from these animals did not seem to be affected by whether or not the sows had ovulated at the time of slaughter.

Before insemination, the sperm had a good viability as shown in Table 1. No differences were observed between the semen of the two boars tested. After mixing the semen with BTS-Caf/Ca, most of the spermatozoa displayed a more continuous motility.

TABLE 1

Viability of sperm in the semen preparations after storage overnight (n = 3)

| Inseminate | % Motile sperm | % NAR[1] | % LAC[2] |
| --- | --- | --- | --- |
| 1. BTS (reference) | 74 (±5) | 74.3 (±4.5) | 4.7 (±1.5) |
| 2. Sperm in BTS, mixed with an equal volume of BTS-Caf/Ca | 75 (±1) | 75.6 (±1.5) | 5.3 (±1.2) |
| 3. BTS + excess EDTA | 67 (±13) | 78.7 (±1.2) | 4.3 (±1.2) |

TABLE 1-continued

Viability of sperm in the semen preparations after storage overnight (n = 3)

| Inseminate | % Motile sperm | % NAR[1] | % LAC[2] |
| --- | --- | --- | --- |

Means (±Standard Deviation) of the 3 ejaculates used observations.
[1]Sperm with a normal apical ridge.
[2]Sperm with a loose or lost acrosomal cap.

Most of the semen back flow (70–80%) was collected within the first hour after insemination. After insemination with sperm in regular BTS, the volume of the recovered liquid, without urine contamination, varied from 60 to 120% of the inseminated volume. Less variation was observed after insemination with sperm in BTS and BTS-Caf/Ca, whereas considerably more variation was observed after insemination with sperm in BTS-EDTA.

The neutrophils were distinguished from other leukocytes in wet mounts by phase-contrast microscopy. A good correlation was found with differential stained smears according to May-Grunwald/Giemsa. More than 95% of the leukocytes in the back flow and in the rinse fluid of the uterus were neutrophils. The percentage of neutrophils in the back flow was not influenced by the composition of the inseminate or by whether or not ovulation had occurred at the time of slaughter. In the cervix and vagina the proportion of neutrophils had more variation and was somewhat lower (70–90%), especially in sows inseminated with sperm in BTS+BTS-Caf/Ca (about 40%).

The brightly fluorescent nuclei of the H33342-stained spermatozoa were clearly observed inside the phagocyte and in the tissue homogenates.

PMN Recruitment.

The numbers of total recovered PMNs per sow differed markedly between the individual animals. PMN recruitment was not correlated with age or parity of the sow. The total numbers of PMNs did not differ significantly between the inseminations of sperm in usual BTS and in BTS-EDTA, whereas after insemination with semen in BTS and in BTS+BTS-Caf/Ca, the recruitment was significantly reduced (p<0.01) (Table 2). In the animals inseminated with regular semen or with semen plus BTS-Cafeine/Ca, almost 50% of the total recruited PMN was found in the back flow. In contrast, animals inseminated with semen in BTS-EDTA, the total recruited PMN in the back flow was only 20%.

TABLE 2 mean number of PMN recovered, ± s.e.

| | Backflow | Back flow + Genital tract |
| --- | --- | --- |
| Regular BTS (n = 6) | 2.16 (±0.70) | 4.44 (±1.19) |
| BTS-Caf/Ca (n = 5) | 0.59 (±0.40) | 1.33 (±0.71) |
| BTS-EDTA (n =6) | 1.25 (±0.53) | 5.59 (±1.33) |

Sperm Recovery.

Like the number of recruited PMN, the total number of recovered sperm per sow varied between the individual animals. This variation was more marked after insemination with semen in BTS-EDTA. No significant differences were found in the total number of recovered sperm between the sows inseminated with semen of boar A or boar B. Spermatozoa were found in all oviducts irrespective of the composition of the inseminate.

In all three treatment groups, the total number of sperm recovered at four hours after insemination (i.e., inside plus outside PMN, in the back flow plus the genital tract) was approximately 50% of the number of sperm inseminated (Table 3).

TABLE 3

Number* of recovered sperm.

|  | Backflow | Genital tract | Total |
|---|---|---|---|
| Regular BTS (n = 6) | 43.1 (±8.9) | 5.2 (±1.9) | 48.7 (±7.3) |
| BTS-Caf/Ca (n = 5) | 31.8 (±6.2) | 18.8 (±4.2) | 51.7 (±9.0) |
| BTS-EDTA (n = 6) | 37.7 (±8.4) | 9.3 (±2.6) | 47.4 (±7.3) |

Mean ± SE
*expressed as a percentage of number of sperm in the inseminate.

The total number of sperm in the genital tract (i.e., within the genital tract and outside PMN) was significantly ($p<0.01$) higher in the BTS+BTS-Caf/Ca group when compared to the regular BTS group (Table 3). Moreover, a significantly lower proportion of these spermatozoa were found inside PMN (table 4). The number of free, non-phagocytosed sperm in the uterus was much higher (highly significant $P<0.001$) in the BTS+BTS-Caf/Ca group when compared to the regular BTS group (Table 5). At four hours after insemination, the number of sperm in the oviducts was not higher in the BTS±BTS-Caf/Ca group (table 5).

TABLE 4

Percentage of sperm found inside PMN at 4 hours after insemination.

| Inseminate | Back flow | Vagina/Cervix | Uterus |
|---|---|---|---|
| BTS | 21.5 (±5.8) | 73.5 (±6.7) | 66.5 (±10.0) |
| BTS + caffeine/Ca$^{2+}$ | 15.1 (±6.1) | 48.5 (±8.6)* | 28.6 (±10.5)* |
| BTS + excess EDTA | 32.1 (±6.8) | 78.3 (±6.6) | 84.8 (±7.5) |

Mean (±SE)
*Value differed significantly from that of the regular BTS group ($p<0.05$).

TABLE 5

Number* of free, non-phagocytosed sperm in uterus and oviducts PMN at 4 hours after insemination.

|  | Uterus | Oviducts |
|---|---|---|
| Reference | 1.07 (±0.16) | 0.0071 (±0.0016) |
| Caffeine/calcium | 14.95 (±3.11) | 0.0040 (±0.0014) |
| Excess EDTA | 1.38 (±0.36) | 0.0026 (±0.0010) |

Mean (±SE)
*expressed as a percentage of number of sperm in the inseminate.

As to semen back flow and sperm recovery in the uterus, the differences between the BTS-EDTA group and the regular BTS group were small and not significant. The sperm recovery in the oviducts was significantly lower in the BTS-EDTA group($p<0.05$). Observations in the individual animals revealed some remarkable extremes. In two sows, 87% and 75% of the inseminated sperm was recovered in the back flow, respectively, whereas in two other animals, this was only 4% and 3%, respectively. In only one of the two latter animals did the reduced back flow coincide with a slightly higher number of non-phagocytized sperm in the uterus.

The results show that the use of caffeine in combination with Ca$^{2+}$ significantly reduced PMN recruitment during the first four hours after insemination. Also, the use of caffeine/Ca$^{2+}$ drastically enhanced the number of free, not-phagocytosed sperm that were still present in the uterus at four hours after insemination, indicating that phagocytosis of sperm had been seriously reduced. Without being bound thereto, it is possible that the reduction of phagocytosis is partly due to an effect on the spermatozoa that results in a reduced rate of phagocytosis by PMN as was found earlier in in vitro experiments, and partly due to the reduced number of PMN present in the genital tract.

Both effects are due to the action of caffeine as an inhibitor of phosphodiesterase.

The in vitro phagocytosis experiments did show that phagocytosis of sperm by PMN was indeed decreased by addition of caffeine, especially when used in combination with Ca$^{2+}$. This effect, however, was due to some action of the active compounds on the spermatozoa and not to an effect on the PMN.

It has been shown that treatment of sperm for in vitro capacitation also considerably reduces the rate of phagocytosis of sperm by PMN. The effect of caffeine/Ca$^{2+}$ on phagocytosis of sperm in vitro does not come down to a stimulation of capacitation. In at least some of the in vitro experiments in which the effect of caffeine on phagocytosis of sperm was shown, the sperm were not washed free of the seminal plasma. Seminal plasma is known to inhibit sperm phagocytosis. Furthermore, the effect of caffeine was seen without added calcium ions and in the presence of EDTA, which totally inhibits sperm capacitation (Harkema et al. 1998). On the other hand, it was noted that calcium ions augment the effect of caffeine.

In the present invention, the use of caffeine/Ca$^{2+}$ did not result in a higher number of sperm present in the oviducts. The passage of the sperm from the uterus to the oviducts, the so-called utero-tubal junction, seems to be designed to keep access of sperm to the oviducts at a very low level. This is suggested to be vital for the prevention of polyspermy. The sperm population in the oviducts is reported to continue to grow during the first 24 hours after insemination due to the continued passage of sperm from the uterus (Pursel, et al. 1978). Consequently, the higher number of sperm found to be present in the uterus after insemination with caffeine/Ca$^{2+}$ is favorable for the chance of fertilization, especially when the interval between insemination and ovulation is increased. Moreover, the fact that caffeine/Ca$^{2+}$ decreases the elimination of sperm from the genital tract shows that the same uterus sperm population achieved with "normal" inseminations in regular BTS can be achieved with a substantial lower number of sperm in the inseminate when using BTS plus caffeine/Ca$^{2+}$.

In in vitro experiments, another way to reduce phagocytosis of sperm in vitro was found to be lowering the free Ca$^{2+}$ concentration by EDTA.

However, in the present in vivo study, insemination with semen in BTS with excess sodium EDTA had no positive effects. Neither recruitment of PMN nor the extent of elimination of sperm from the genital tract was attenuated. It is suggested that as soon as the inseminate fluid containing the EDTA is expelled, and Ca$^{2+}$ and other metal ions become available from uterine mucus, wherein the PMN could still start with a rapid ingestion of sperm. Since the presence of EDTA would also have retarded the process of capacitation these spermatozoa would be especially vulnerable for phagocytosis. Indeed, it turned out that the presence of extra EDTA in the inseminate had a negative effect on the number of sperm in the oviducts.

EXAMPLE III

Caffeine plus Ca$^{2+}$ reduces uterine leukocyte recruitment and sperm phagocytosis and improves fertility in pig AI.

Within hours after insemination, the number of sperm in the female genital tract is dramatically reduced due to phagocytosis of sperm by uterine PolyMorphoNuclear leukocytes PMN (Pursel, V. G., et al. (1978) Biol. Reprod. 19: 69–76), which are recruited in vast numbers to the lumen of the uterus shortly after AI. Caffeine (plus $CaCl_2$) markedly reduces the rate of sperm phagocytosis in vitro. The effect of caffeine on PMN recruitment, numbers of not-phagocytosed sperm in the genital tract, the percentage of fertilized oocytes, and the number of accessory sperm is measured.

Materials and Methods.

Series 1: Batches of sows (parity 3–12) received hCG at 96 hours after weaning. Sows showing oestrus were inseminated 26 hours after hCG with H33342 labeled semen with either $1 \times 10^9$ sperm in 80 ml normal BTS extender or with $1 \times 10^9$ sperm in 40 ml normal BTS followed by 40 ml of BTS minus EDTA and with 6 mM $CaCl_2$ and 2,3 mM caffeine. Semen backflow was collected using stoma bags around the vulva. The animals were slaughtered at four hours after insemination. Vagina, cervix and uterus were flushed repeatedly with PBS. Sperm and PMN were counted in the flushings and the backflow. The tractus parts, including the oviducts, were homogenized to count the remaining sperm.

Series 2: Batches of sows (parity 2–13) received hCG at 84 hours after weaning. The sows were inseminated at 16 hours after hCG administration (on average 26 hours, ranging from 21–28 hours, before ovulation as observed by transrectal ultrasonography) or inseminated at 4 hours after ovulation. The sows were inseminated with $0.5 \times 10^9$ sperm in 40 ml normal BTS followed by 40 ml of normal BTS or BTS minus EDTA and plus 6 mM $CaCl_2$ and 2.3 mM caffeine. The sows were slaughtered at 115 (112–120) hours after ovulation. The embryos were flushed, examined morphologically, and the number of accessory sperm were counted.

Results and Discussion.

The use of caffeine/$CaCl_2$ significantly reduced PMN recruitment and resulted in significantly higher number of sperm in the uterus (P<0.01) at 4 hr. after AI. Oviduct sperm number was not significantly different. Caffeine/$CaCl_2$ resulted in a significantly higher number of accessory sperm in the sows inseminated 26 hours before ovulation. The % fertilized oocytes tended to be higher with caffeine (not significant).

The addition of Caffeine/$CaCl_2$ reduces the rate at which sperm are eliminated from the genital tract. The improved fertility at 26 hours after AI shows that the number of sperm in the oviducts remains longer at a sufficient level, which could have consequences for field fertility in pig AI and/or could enable a reduction of sperm dosage.

Series 1.

|  | Control | Caffeine/Ca |
|---|---|---|
| Number of sperm ($\times 10^6$) | | |
| Inseminated | 1150 | 1080 |
| Backflow[1] | 495 ± 75 | 313 ± 92 |
| Total in tractus[1] | 58 ± 14 | 216 ± 72 |
| Uterus[2] | 13 ± 1.1 | 162 ± 77 |
| Oviducts[2] | 0.08 ± 0.03 | 0.04 ± 0.01 |
| Number of PMN ($\times 10^6$) | | |
| Total tract + backflow | 4458 ± 1029 | 1327 ± 593 |

[1]including sperm inside PMN.
[2]only free, not-phagocytosed sperm

Series 2.

|  | AI ± 26 hrs before ovulation | | AI ± hrs after ovulation | |
|---|---|---|---|---|
|  | Control n = 16 | Caffeine/Ca n = 16 | Control n = 16 | Caffeine/Ca n = 17 |
| % norm. Embryos[1] | 89.9 | 96.4 | 98.5 | 100 |
| # of accessory sperm[2] | 5.8[a] | 16.2[bc] | 44.6[c] | 41.9[c] |
| # of cells per embryo[1] | 39 ± 11 | 52 ± 26 | 35 ± 9 | 38 ± 12 |

[1]not significant.
[2] a,b,c significantly different (P<0.001).

EXAMPLE IV

Influence of treatment for in vitro capacitation of boar sperm on ocytosis by PMN.

| Time (min.) | % sperm phagocytosed Non-capacitated | Capacitated |
|---|---|---|
| 0 | 0 ± 0 | 0 ± 0 |
| 15 | 61 ± 2.5 | 20 ± 2.0 |
| 30 | 70 ± 2.3 | 27 ± 2.3 |
| 45 | 73 ± 2.2 | 33 ± 2.6 |
| 60 | 77 ± 2.0 | 35 ± 2.5 |
| 75 | 78 ± 2.0 | 35 ± 2.5 |
| 90 | 81 ± 1.9 | 41 ± 2.8 |

% sperm phagocytosed by PMN in vitro, mean (n = 3) ± s.e.

What is claimed is:

1. A method for artificially inseminating a subject, said method comprising:
   obtaining sperm;
   obtaining a composition comprising an inhibitor of phosphodiesterase and a calcium salt;
   mixing said sperm with said composition, thus producing an inseminate; and
   administering the inseminate to the subject.

2. The method according to claim 1, wherein the inhibitor of phosphodiesterase is selected from the group consisting of caffeine, theophylline, theobromine, isobutylmethylxanthine, other xanthine based compounds, papaverine, and combinations of any thereof.

3. The method according to claim 1, wherein an amount of the inhibitor of phosphodiesterase comprises up to 10 mmol per liter of said inseminate.

4. The method according to claim 1, wherein a concentration of the calcium salt comprises up to 10 mmol per liter of said inseminate.

5. The method according to claim 1, wherein:
   the calcium salt comprises calcium chloride; and
   a concentration of the calcium chloride comprises an amount of about 0.1 to 8 mmol per liter of said inseminate.

6. The method according to claim 1, wherein the subject is a mammal or a bird.

7. The method according to claim 5, wherein the subject is a pig.

8. A method for reducing phagocytosis of sperm in a female genital tract, said method comprising:
   obtaining sperm;

obtaining a solution comprising an inhibitor of phosphodiesterase and a calcium salt;

admixing said sperm with said solution for inseminating a subject.

9. The method according to claim 8, wherein the inhibitor of phosphodiesterase is caffeine.

10. The method according to claim 8, wherein the calcium salt is calcium chloride.

11. In a method of artificially inseminating a subject with an inseminate, the improvement comprising admixing a phosphodiesterase inhibitor and a calcium salt with the inseminate, wherein the inseminate comprising the phosphodiesterase inhibitor and the calcium salt is capable of inhibiting phagocytosis of the sperm as determined by a phagocytosis assay.

12. The method according to claim 11, wherein the phosphodiesterase inhibitor is selected from the group consisting of caffeine, theophylline, theobromine, isobutylmethylxanthine, other xanthine based compounds, papaverine, and combinations of any thereof.

13. A method for artificially inseminating a subject, said method comprising:

obtaining an inseminate consisting essentially of sperm, an inhibitor of phosphodiesterase and a calcium salt; and administering the inseminate to the subject.

14. The method according to claim 13, wherein the phosphodiesterase inhibitor is selected from the group consisting of caffeine, theophylline, theobromine, isobutylmethylxanthine, other xanthine based compounds, papaverine, and combinations of any thereof.

15. The method according to claim 13, wherein the inseminate is capable of inhibiting phagocytosis of the sperm as determined by a phagocytosis assay.

16. The method according to claim 1, wherein the inseminate is capable of inhibiting phagocytosis of the sperm as determined by a phagocytosis assay.

* * * * *

UNITED STATES PATENT AND TRADEMARK OFFICE
CERTIFICATE OF CORRECTION

PATENT NO. : 6,890,708 B2  Page 1 of 1
APPLICATION NO. : 10/277165
DATED : May 10, 2005
INVENTOR(S) : Jacoba Johanna Matthijs-Rijsenbilt and Henri Woelders It is certified that error appears in the above-identified patent and that said Letters Patent is hereby corrected as shown below:

On the title page:
In ITEM (56) References Cited    change "Abbydeera et al.," to --Abeydeera et al.,--
OTHER PUBLICATIONS line 1    change "Theriogenology, 1997, pp. 537-534," to --Theriogenology, 1997, pp. 537-544,--

Signed and Sealed this

Sixteenth Day of December, 2008

JON W. DUDAS
*Director of the United States Patent and Trademark Office*